(12) United States Patent
Wada et al.

(10) Patent No.: US 6,498,283 B1
(45) Date of Patent: Dec. 24, 2002

(54) BODY FLUID ABSORBENT GARMENT

(75) Inventors: Ichiro Wada, Kagawa-ken (JP); Kozo Abe, Kagawa-ken (JP); Noriyuki Kurita, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 50 days.

(21) Appl. No.: 09/713,004

(22) Filed: Nov. 16, 2000

(30) Foreign Application Priority Data

Nov. 17, 1999 (JP) .......................................... 11-326806

(51) Int. Cl.⁷ ................................................ A61F 13/15
(52) U.S. Cl. .................. 604/378; 604/358; 604/385.01; 604/379; 604/380
(58) Field of Search ................................ 604/358–402, 604/317, 385.01

(56) References Cited

U.S. PATENT DOCUMENTS 4,685,915 A 8/1987 Hasse et al.
5,613,959 A * 3/1997 Roessler et al. ............ 604/364
5,674,213 A 10/1997 Sauer
5,827,254 A 10/1998 Trombetta et al.
5,830,202 A 11/1998 Bogdanski et al.

FOREIGN PATENT DOCUMENTS

| DE | 199 15 716 | 8/2000 |
| EP | 0 442 223 | 8/1991 |
| JP | 1994-21626 | 3/1994 |
| WO | 97 34559 | 9/1997 |
| WO | 98 37847 | 9/1998 |
| WO | 99 25297 | 5/1999 |

* cited by examiner

Primary Examiner—Jeanette Chapman
(74) Attorney, Agent, or Firm—Lowe Hauptman Gilman & Berner, LLP

(57) ABSTRACT

A body fluid absorbent garment includes a topsheet, a backsheet and a core disposed therebetween, the core is formed with a pair of protruding barriers spaced from each other and extending parallel to the side edges and has a density lower in the protruding barriers than in its zone free from formation of the protruding barriers.

22 Claims, 7 Drawing Sheets

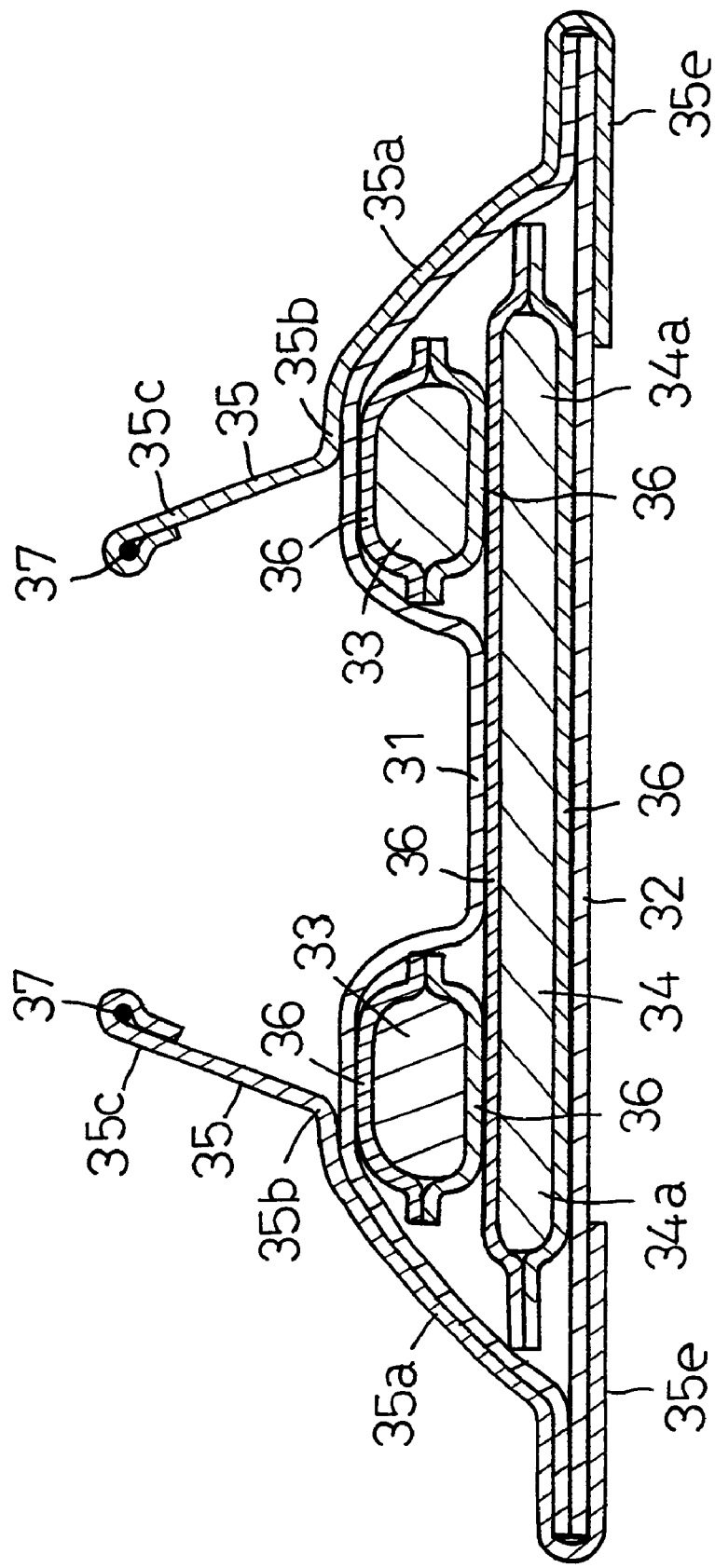

BODY FLUID ABSORBENT GARMENT

BACKGROUND OF THE INVENTION

This invention relates to a body fluid absorbent garment adapted for absorbing and containing of body fluids discharged thereon, such as disposable diapers, urine absorbent pads for incontinent, diaper liners, panty liners or sanitary napkins.

Japanese Utility Model Application Disclosure No. 1994-21626 describes a disposable diaper comprising a liquid-pervious topsheet, a liquid-impervious backsheet and a liquid-absorbent core disposed between these two sheets. A pair of absorbent auxiliary members transversely spaced from each other and longitudinally extend on the topsheet at least in a crotch region so that these auxiliary members may protrude upwardly of the core and have a compressive modulus higher than that of the core. Such high compressive modulus ensures these auxiliary members to fit to a wearer's skin and to prevent excretion from leaking sideways even when the auxiliary members are deformed under a wearer's body weight since the auxiliary members can rapidly restore their initial positions and function to absorb or barrier off excretion.

If a relatively large amount of urine is discharged, a rate of urination will exceed a rate at which the core is capable to absorb urine. As a result, an amount of urine staying on the upper surface of the core may flow backward and cause undesirable leak. The diaper disclosed in the above-identified Disclosure includes no means promoting urine to spread over the entire surface zone of the core defined between the auxiliary members. If the amount of discharged urine is too large to be absorbed by the auxiliary members themselves, the rest amount of urine may stay on the core at its zone onto which urine is discharged, then spread and leak outward sideways beyond the respective auxiliary members. Furthermore, if the amount of urine absorbed by the auxiliary members can not be smoothly transferred into the core, such amount of urine staying in the auxiliary members may exude as the auxiliary members are collapsed under the wearer's body weight.

SUMMARY OF THE INVENTION

The object of this invention is to provide a body fluid absorbent garment including a liquid-absorbent core formed with a pair of protruding barriers adapted to barrier off liquid excretion such as loose passage, urine or menstrual discharge so that such liquid excretion may rapidly spread over the entire surface zone of the core defined between the protruding barriers and be absorbed from the surface zone into the core well before undesirable leak of excretion might occur.

The object of this invention is also to provide a body fluid absorbent garment ensuring that the amount of excretion having been absorbed by the protruding barriers to be smoothly transferred into the core without any possibility that the amount of excretion might exude from the protruding barriers.

According to this invention, there is provided a body fluid absorbent garment having transversely opposite and longitudinally extending side edges and longitudinally opposite and transversely extending ends, comprising: a liquid-pervious topsheet; a liquid-impervious backsheet; a liquid-absorbent core disposed therebetween; the core being formed on a side thereof immediately underlying the topsheet with a pair of protruding barriers spaced from each other along at least said transversely opposite side edges of said transversely opposite side edges and said longitudinally opposite ends; and the protruding barriers having a density lower than that of the core in a base zone thereof free from formation of the protruding barriers.

With the body fluid absorbent garment according to this invention, excretion rapidly spreads over the surface of the core and is rapidly absorbed by the core in its zone other than its protruding zones. Even if a relatively large amount of excretion is locally discharged onto the garment, it is not apprehended that the excretion might stay in such zone onto which the excretion is directly discharged and leak beyond the protruding zones.

The amount of excretion having reached the protruding zones is successively absorbed by these protruding zones before any amount of such excretion might leak sideways beyond the side edges of the garment. The excretion having been absorbed by the protruding zones having a relatively low density is immediately absorbed by the rest zone having a relatively high density and therefore it is not apprehended that the excretion might exude out from the protruding zones even if the protruding zones are collapsed under a wearer's body weight. The protruding zones are more soft than the rest zone and, in addition, have their corners appropriately rounded, so give the wearer no feeling of discomfort as these protruding zones come in contact with the wearer's skin.

BRIEF DESCRIPTION OF THE DRAWINGS

FIG. 7 is a sectional view taken along line B—B in FIG. 6.

DETAILED DESCRIPTION OF THE PREFERRED EMBODIMENTS

Details of a body fluid absorbent garment according to this invention will be more fully understood from the description of a disposable diaper and a urine absorbent pad for incontinent as embodiments of this invention given hereunder with reference to the accompanying drawings.

Figure 1:
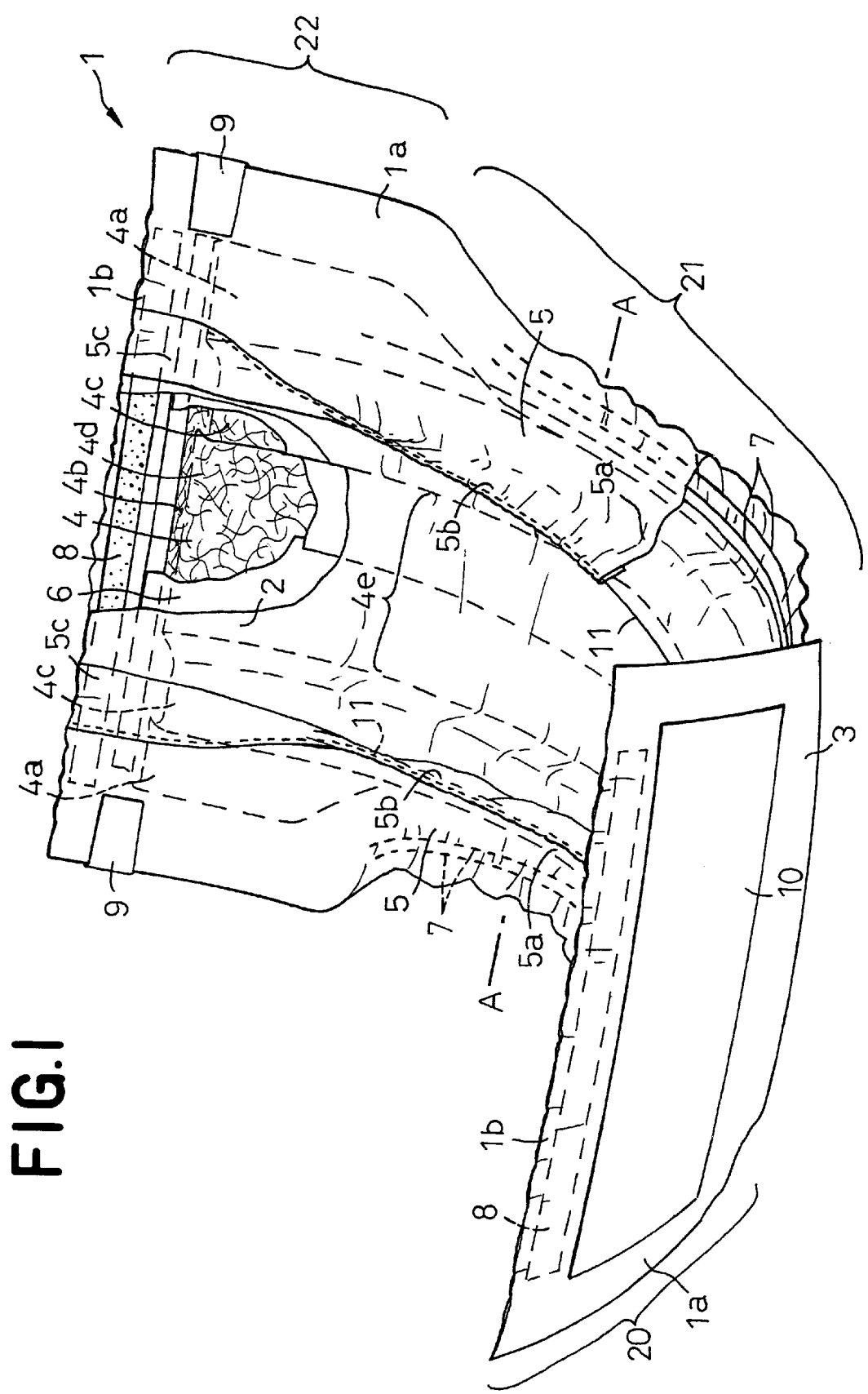
FIG. 1 is a perspective view depicting a partially cutaway disposable diaper according to this invention.
Figure 2:
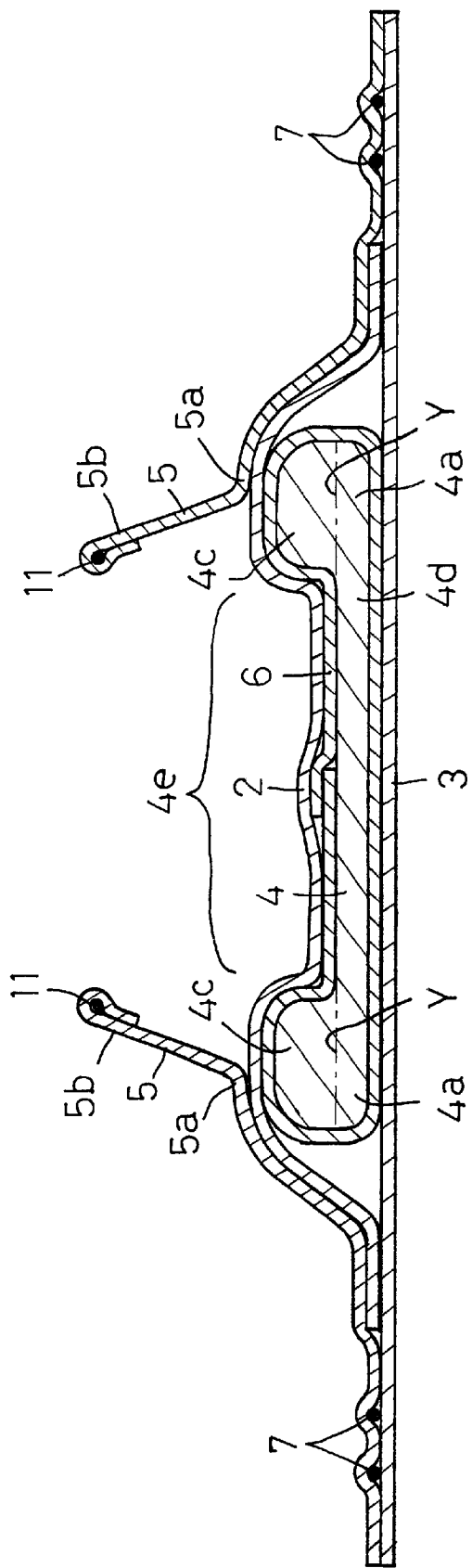
FIG. 2 is a sectional view taken along line A—A in FIG. 1.

FIG. 1 is a perspective view depicting a partially cutaway disposable diaper according to this invention and FIG. 2 is a sectional view taken along line A—A in FIG. 1. Referring to FIG. 2, an imaginary line Y indicates a boundary between a zone of a liquid-absorbent core 4 defining a pair of protruding barriers 4c, 4c and the remaining base zone 4d of the core 4. A diaper 1 comprises a liquid-pervious topsheet 2, a liquid-impervious backsheet 3 and the liquid-absorbent core 4 disposed between these two sheets 2, 3.

The diaper 1 is longitudinally composed of a front waist region 20, a rear waist region 22 and a crotch region 21 extending between these two waist regions 20, 22. The diaper 1 has an hourglass-like shape contoured by transversely opposite side edges 1a, 1a extending longitudinally of the diaper 1 so as to describe circular arc curved inward laterally of the diaper 1 and longitudinally opposite ends 1b, 1b extending transversely of the diaper 1. The diaper 1 is provided on the upper surface of the topsheet 2 with a pair of barrier sheets 5 extending longitudinally of the diaper with the barrier sheets 5 spaced from each other.

The core 4 comprises a mixture of fluff pulp and high molecular water-absorbent polymer particles compressed to a desired thickness and entirely covered with and joined to a water-pervious sheet 6. The core 4 is formed with a pair of protruding barriers 4c, 4c protruding from the upper surface of the core 4 corresponding to the boundary as indicated by the imaginary line Y in FIG. 2 and having their corners appropriately rounded. The protruding barriers 4c, 4c lie on the side edges 4a, 4a of the core 4, respectively, and extend parallel to each other substantially without describing any significant curves. The core 4 has a density lower in these protruding barriers 4c, 4c lower than in the zone 4d free from formation of the protruding zones 4c, 4c. Distribution of the polymer particles in the protruding zones 4c, 4c and the base zone 4d is practically uniform.

A density of the fluff pulp, a component of the core 4 is 0.02~0.10 g/cm$^3$ in the protruding zones 4c, 4c and 0.05~0.20 g/cm$^3$ in the zone 4d, more preferably, 0.05~0.06 g/cm$^3$ in the protruding zones 4c, 4c and 0.10~0.11 g/cm$^3$ in said zone 4d.

In the base zone 4d of the core 4 containing the fluff pulp in the range of density, fiber interstices of the fluff pulp are sufficiently dense to promote a capillarity. With a consequence, excretion can rapidly spread in the base zone 4d not only in a thickness direction of the core 4 but also over the upper surface of the core 4 and can be rapidly absorbed in the base zone 4d.

In the base zone 4d of the core 4, excretion moved down through the topsheet 2 and the water-pervious sheet 6 to the base zone 4d can rapidly spread over an area 4e of the base zone 4d defined between the pair of protruding base zones 4c, 4c and be rapidly absorbed by the core 4 over the area 4e of the base zone 4d.

In the course of spreading over the area 4e of the base zone 4d, the amount of excretion having reached the protruding zones 4c, 4c is successively absorbed by these protruding zones 4c, 4c without any possibility of leaking sideways beyond the side edges 1a, 1a of the diaper 1. In the protruding zones 4c, 4c containing the fluff pulp at a density lower than that in the base zone 4d, the amount of excretion having been absorbed by the protruding zones 4c, 4c are then absorbed by the base zone 4d and therefore it is not apprehended that the amount of excretion might exude from the protruding zones 4c, 4c even when these protruding zones 4c, 4c are collapsed under a wearer's body weight.

The protruding zones 4c, 4c containing the fluff pulp at said range of density are more soft than the base zone 4d and do not give the wearer a feeling of incompatibility as these protruding zones 4c, 4c come in contact with the wearer's skin.

At the density of the fluff pulp in the protruding zones 4c, 4c being less than 0.02 g/cm$^3$, the fiber interstices of the fluff pulp would be reduced under a surface tension of liquid contained in excretion as the latter is absorbed by the protruding zones 4c, 4c and a vertical dimension of these protruding zones 4c, 4c are correspondingly reduced, resulting in a possibility that the excretion might leak out beyond the protruding zones 4c, 4c. At the density of the fluff pulp in the protruding zones 4c, 4c exceeding 0.10 g/cm$^3$, on the other hand, a differential density of the protruding zones 4c, 4c and the base zone 4d would be too reduced to ensure a smooth transfer of the excretion having been absorbed by the protruding zones 4c, 4c to the base zone 4d and therefore it is apprehended that the amount of excretion staying in the protruding zones 4c, 4c might exude out from the protruding zones 4c, 4c as these zones 4c, 4c are collapsed under the wearer's body weight.

At the density of the fluff pulp in the base zone 4d being less than 0.05 g/cm$^3$, the excretion could neither rapidly spread over the area 4e of the base zone 4d nor be absorbed entirely over the area 4e of the base zone 4d. At the density of the fluff pulp in the base zone 4d exceeding 0.20 g/cm$^3$, on the other hand, a rigidity of the core 4 in the base zone 4d would correspondingly increase and the core 4 would give the wearer a feeling of discomfort as the core 4 comes in contact with the wearer's skin.

The core 4 may contain, in addition to the fluff pulp and the high molecular water-absorbent polymer particles, staple fibers made of thermoplastic synthetic resin. The core 4 containing such staple fibers comprises a mixture of the fluff pulp, the staple fibers and the polymer compressed to a desired thickness and entirely covered with and joined to a water-pervious sheet 6. The core 4 contains the fluff pulp and staple fibers at a density lower in its protruding zones 4c, 4c than in the base zone 4d free from formation of the protruding zones 4c, 4c. Preferably, the core 4 contains the fluff pulp and the staple fibers as a whole at a density of 0.02~0.10 g/cm$^3$ in the protruding zones 4c, 4c and at a density of 0.05~0.20 g/cm$^3$ in the base zone 4d.

In the base zone 4d of the core 4 containing the staple fibers, fiber interstices of the fluff pulp as well as the staple fibers are sufficiently dense to promote a capillarity. With a consequence, excretion can rapidly spread in the base zone 4d not only in a thickness direction of the core 4 but also over the upper surface of the core 4 and can be rapidly absorbed in the base zone 4d.

In the protruding zones 4c, 4c containing the fluff pulp and the staple fibers as a whole at the density lower than in the base zone 4d, the amount of excretion having been absorbed by the protruding zones 4c, 4c are then immediately absorbed by the base zone 4d.

Along each side edge 1a of the diaper 1, a pair of elastically stretchable members 7, 7 for leg-holes are disposed between the backsheet 3 and the barrier sheet 5 and secured under tension to the inner surface of at least one of the backsheet 3 and barrier sheet 5. Along the longitudinally opposite ends 1b, 1b of the diaper 1, film-like elastically stretchable members 8, 8 for a waist-hole are disposed between the top- and backsheets 2, 3 and secured under tension to the inner surface of at least one of these top- and backsheets 2, 3.

In the rear waist region 22 of the diaper 1, tape fasteners 9, 9 are attached to the side edges 1a, 1a so as to extend laterally inward. In the front trunk region 20 of the diaper 1, a strip of target tape 10 is attached to the outer surface of the backsheet 3 on which said tape fasteners 9, 9 are anchored.

Each of the barrier sheets 5, 5 comprises a fixed side edge portion 5a fixed to the outer surface of the topsheet 2 along the apex of the associated protruding zone 4c of the core 4, a free side edge portion 5b extending parallel to the fixed side edge portion 5a between the longitudinally opposite ends 1b, 1b, and fixed ends 5c laterally outward collapsed and fixed to a portion of the barrier sheet 5 extending laterally outward from the fixed side edge portion 5a. A longitudinally extending elastically stretchable member 11 is secured under tension to the free side edge portion 5b so that the member 11 is wrapped with the outermost portion of the free side edge portion 5b.

The fixed side edge portions 5a, 5a of the respective barrier sheets 5, 5 lie on the apices of the respective protruding zones 4c, 4c. Such a unique arrangement allows the protruding zones 4c, 4c to cooperate with the free side edge portions 5b, 5b of the respective barrier sheets 5, 5 to form sufficiently high barriers to prevent the excretion from leaking sideways even when a width of each barrier sheet 5 defined between the fixed side edge portion 5a and free side edge portion 5b is narrower than that in the case of the core 4 formed with none of the protruding zones 4c, 4c.

FIG. 1 illustrates the diaper 1 as being longitudinally curved with its inner surface inside so that the free side edges 5b, 5b of the respective barrier sheets 5, 5 may rise on the topsheet 2 under contraction of the elastic members 11 provided on these free side edge portions 5b, 5b. Contraction of the respective elastic members 7, 8, 11 generates gathers along the transversely opposite side edges 1a, 1a, the longitudinally opposite ends 1b, 1b of the diaper 1 as well as along the free side edges 5b, 5b of the respective barrier sheets 5.

In the vicinity of the transversely opposite side edges 1a, 1a of the diaper 1, the top- and backsheets 2, 3 and the respective barrier sheets 5 extend laterally outward beyond transversely opposite side edges 4a, 4a of the core 4 and, in extensions of these sheets 2, 3, 5 placed one upon another, the inner surface of the topsheet 2 is joined to the inner surface of the backsheet 3 while the outer surface of the topsheet 2 is joined to the inner surface of the barrier sheets 5, 5. Portions of the backsheet 3 and the barrier sheets 5, 5 further extending laterally outward beyond the side edges of the topsheet 2 have their inner surfaces joined to each other.

In the vicinity of the longitudinally opposite ends 1b, 1b of the diaper 1, the top- and backsheets 2, 3 extend longitudinally outward beyond longitudinally opposite ends 4b, 4b of the core 4 and, in their extensions placed upon each other, 1the inner surface of the topsheet 2 is joined to the inner surface of the backsheet 3. The water-pervious sheet 6 is joined to the inner surface of at least one of the top- and backsheets 2, 3.

Figure 3:
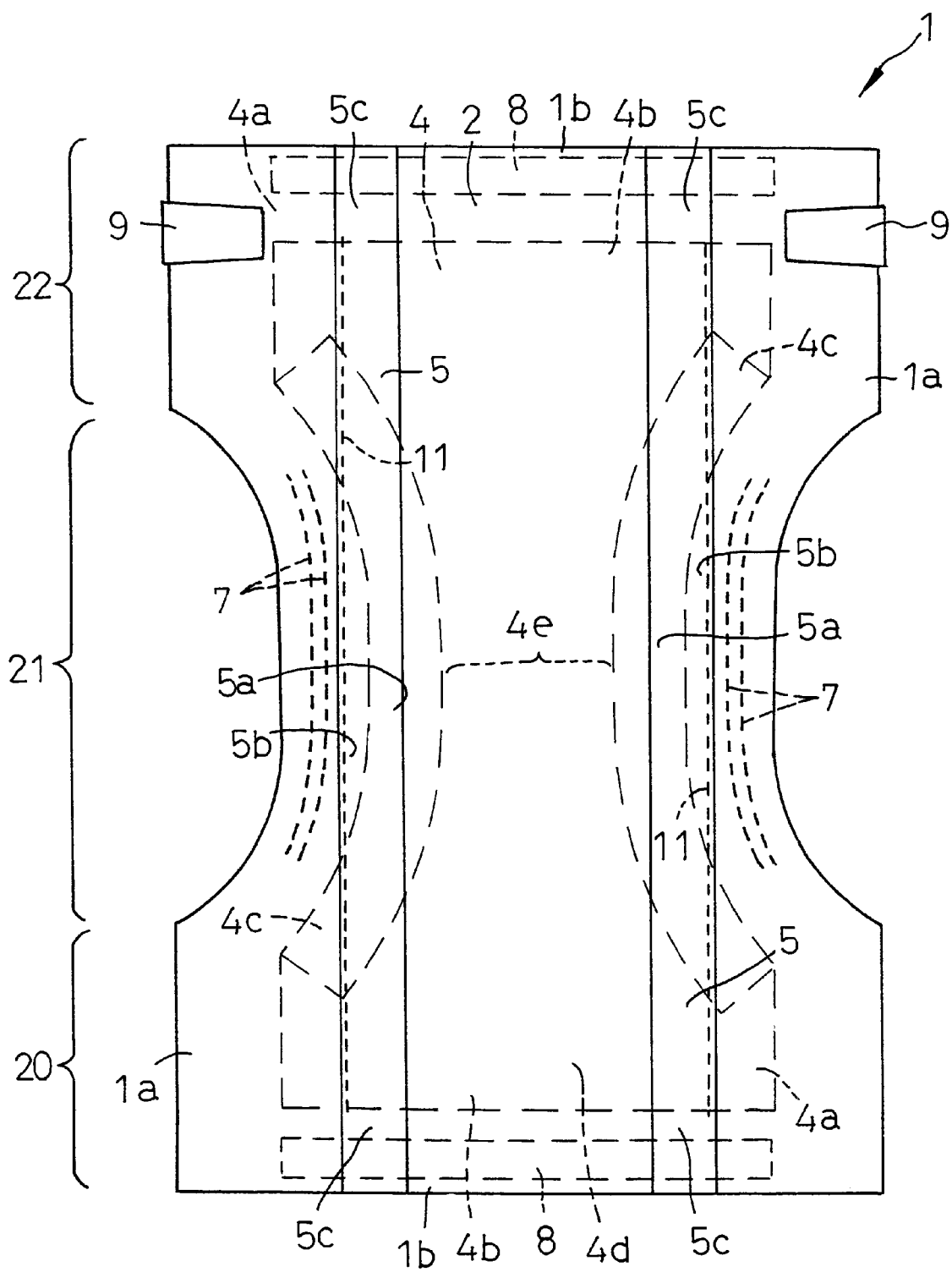
FIG. 3 is a plan view depicting another embodiment of the diaper according to this invention.
Figure 4:
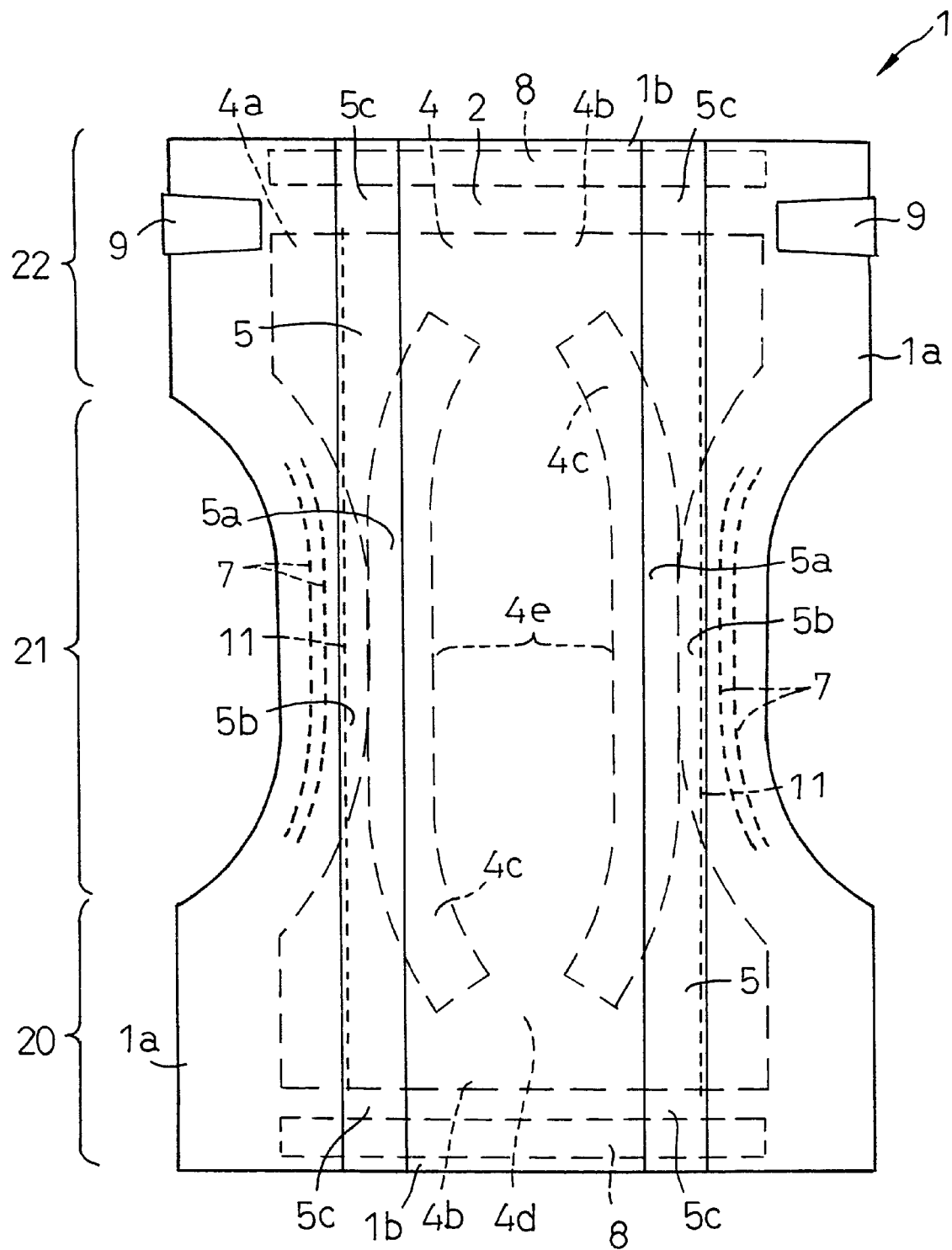
FIG. 4 is a view similar to FIG. 3 depicting still another embodiment of the diaper according to this invention.
Figure 5:
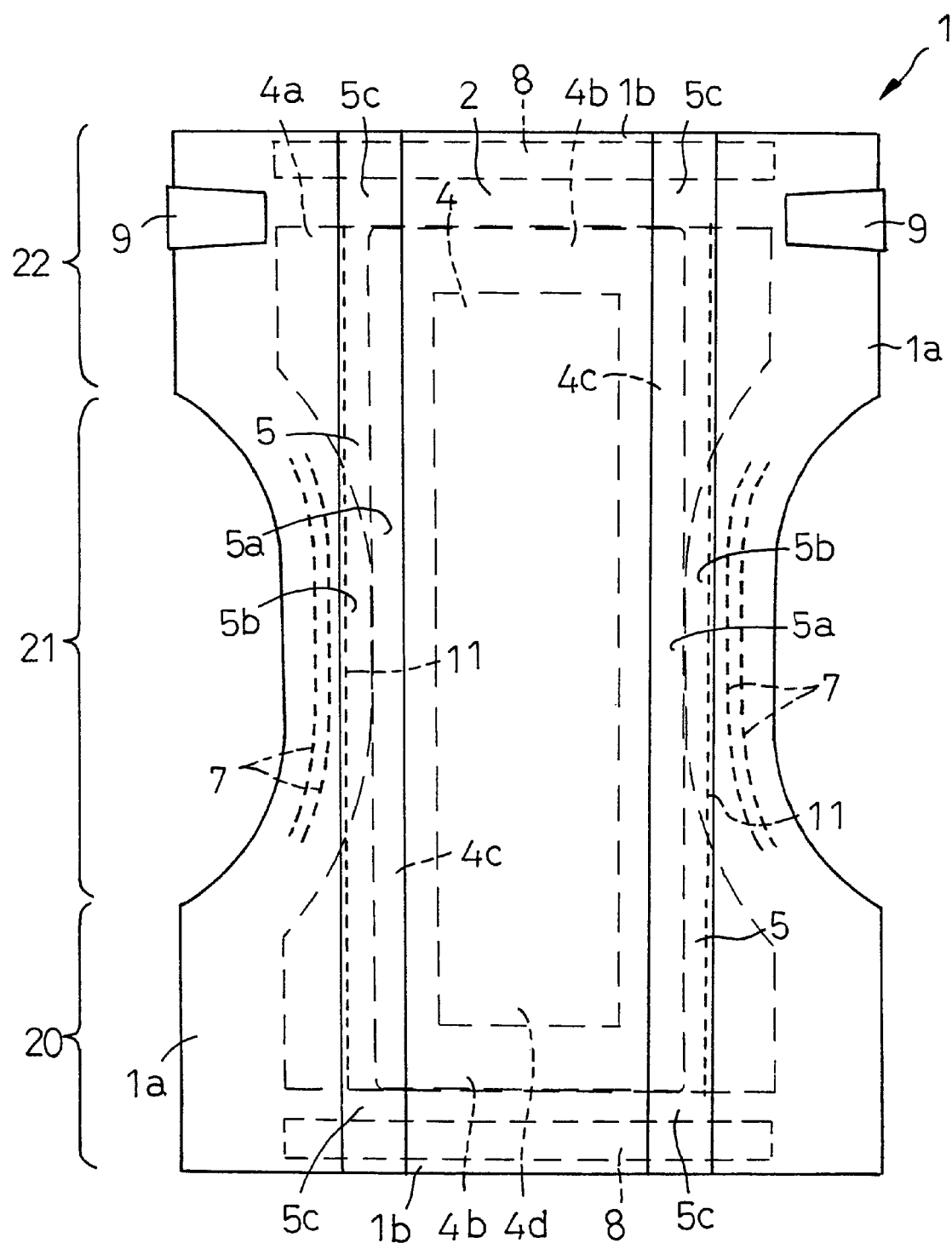
FIG. 5 is a view similar to FIG. 3 depicting further another embodiment of the diaper according to this invention.

FIGS. 3~5 are plan views depicting various alternative embodiments of the diaper as viewed from the side of the topsheet 2. A diaper 1 shown in FIGS. 3~5 is similar to the diaper 1 depicted in FIG. 1 in its basic arrangement. Specifically, the diaper 1 comprises the topsheet 2, the backsheet 3 and the core 4 disposed between these two sheets 2, 3. The diaper 1 is longitudinally composed of the front waist region 20, the rear waist region 22 and the crotch region 21 extending between these two waist regions 20, 22 and is contoured as a whole by the transversely opposite side edges 1a, 1a extending longitudinally of the diaper 1 so as to describe circular arc curved inward laterally of the diaper 1 and the longitudinally opposite ends 1b, 1b extending transversely of the diaper 1. This diaper 1 also is provided along the side edges 1a, 1a of the diaper 1 with the pair of barrier sheets 5, 5 on the side of the topsheet 2.

Referring to FIG. 3, this diaper 1 differs from the diaper 1 of FIG. 1 in that the protruding zones 4c, 4c of the core 4 spaced from each other are curved inward laterally of the diaper 1 in the crotch region 21 to describe circular arcs so that a space between the protruding zones 4c, 4c is larger in the front and rear waist regions 20, 22 than in the crotch region 21. The diaper 1 of FIG. 3 is advantageous in that the protruding zones 4c, 4c are smoothly received in the wearer's crotch and a bulkiness of the core 4 in the crotch region 21 can be alleviated.

The diaper 1 of FIG. 4 is characterized in that the protruding zones 4c, 4c spaced from each other are curved outward laterally of the diaper in the crotch region 21 to describe circular arcs so that a space between the protruding zones 4c, 4c is larger in the crotch region 21 than in the front and rear waist regions 20, 22. The diaper 1 of FIG. 4 is advantageous in that the relatively large space between the protruding zones 4c, 4c in the crotch region 21 enables the excretion to be rapidly spread and absorbed in the area 4e defined between the protruding zones 4c, 4c in the crotch region 21 and thereby to prevent any amount of excretion from leaking sideways in the crotch region 21.

In the case of the diaper 1 shown in FIG. 5, the protruding zones 4c, 4c of the core 4 extend along a peripheral edge of the core 4 to describe a loop. In other words, the protruding zones 4c, 4c form effective barriers not only along the transversely opposite side edges 1a, 1a but also along the longitudinally opposite ends 1b, 1b of the diaper 1 and thereby prevent any amount of excretion from leaking in the vicinity of the transversely opposite side edges 1a, 1a as well as of the longitudinally opposite ends 1b, 1b of the diaper 1.

Figure 6:
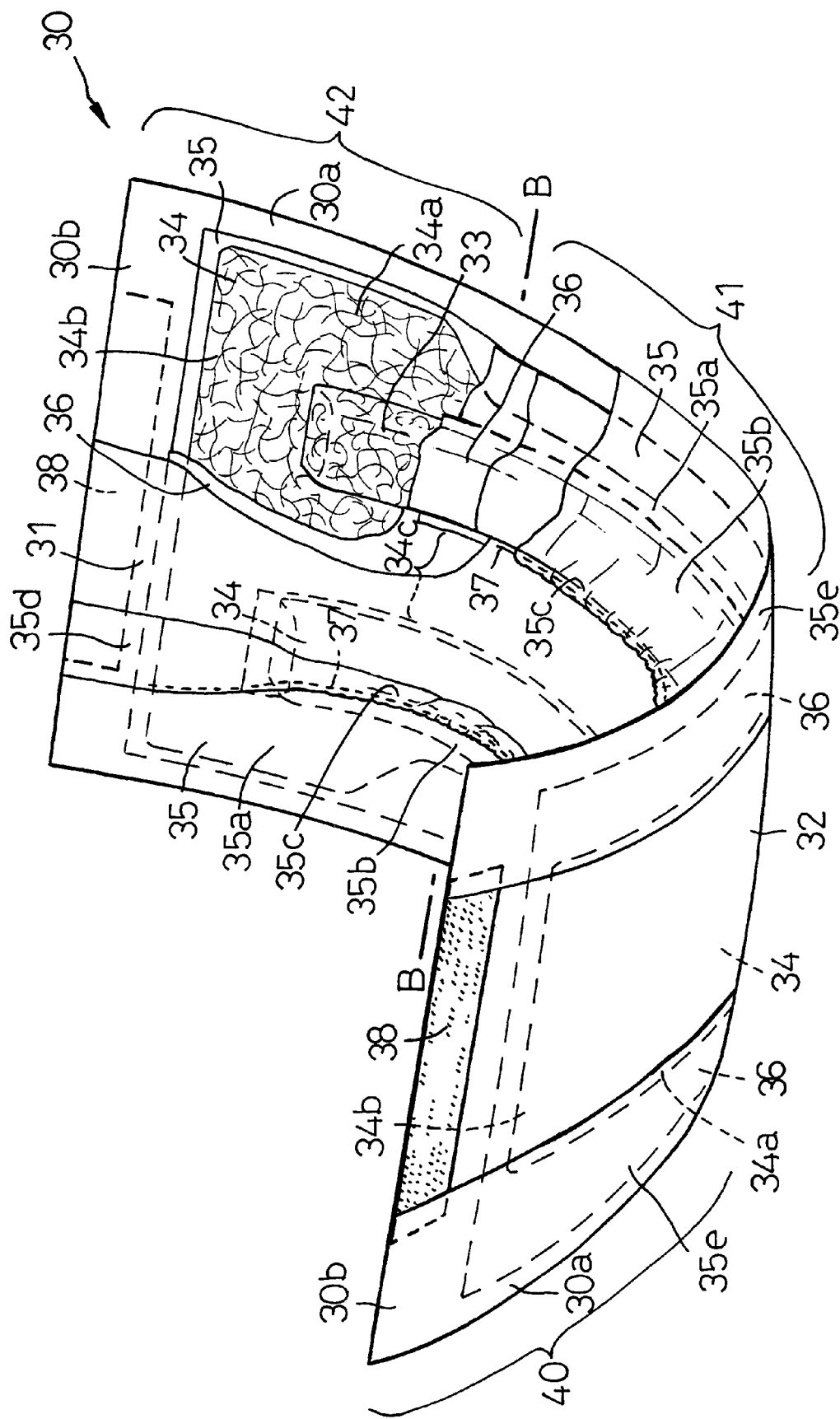
FIG. 6 is a perspective view depicting a partially cutaway urine absorbent pad for incontinent according to this invention.

FIG. 6 is a perspective view depicting a partially cutaway urine absorbent pad 30 for incontinent according to this invention and FIG. 7 is a sectional view taken along line B—B in FIG. 6. The pad 30 comprises a liquid-pervious topsheet 31, a liquid-impervious backsheet 32 and liquid-absorbent cores 33, 34 both disposed between the top- and backsheets 31, 32. The pad 30 is adapted to be attached to the inner surface of an outer sheet such as a diaper cover or an outer sheet of pants for incontinent in actual use.

The pad 30 is longitudinally composed of a front waist region 40, a rear waist region 42 and a crotch region 41 extending between these front and rear waist regions 40, 42, and contoured as a whole by transversely opposite side edges 30a, 30a extending longitudinally of the pad 30 and longitudinally opposite ends 30b, 30b extending transversely of the pad 30. A pair of liquid-barrier sheets 35 spaced from each other and extending longitudinally of the pad 30 are attached to the pad 30 along its side edges 30a, 30a.

The core assembly 33, 34 comprise the lower layer core 34 and the upper layer cores 33, 33 extending almost rectilinearly along transversely opposite side edges 34a, 34a of the lower layer core 34. The upper layer cores 33, 33 have their corners appropriately rounded and extend to the points adjacent longitudinally opposite ends 34b, 34b of the lower layer core 34. The upper layer cores 33, 33 define protruding zones of the lower layer core 34. Both the upper layer cores 33, 33 and the lower layer core 34 comprise mixtures of fluff pulp and high molecular water-absorbent polymer particles compressed to respective desired thickness and entirely covered with and bonded to respective water-pervious sheets 36.

The lower layer core 34 has its area in the front waist region 40 substantially equal to its area in the crotch region 41 and has its area in the rear waist region 42 larger than the total area in the front waist region 40 and the crotch region 41. The upper layer cores 33, 33 contain the fluff pulp at a density lower than a density at which the lower layer core 34 contains the fluff pulp. The amount of polymer particles contained in the upper layer cores 33, 33 and the lower layer core 34 is substantially uniform.

In the case of the pad 30, the upper layer cores 33, 33 contain the fluff pulp at a density of 0.02~0.10 g/cm$^3$ and the lower layer core 34 contains the fluff pulp at a density of 0.05~0.20 g/cm$^3$. More preferably, the upper layer cores 33, 33 contain the fluff pulp at a density of 0.05~0.06 g/cm$^3$ and the lower layer core 34 contains the fluff pulp at a density of 0.10~0.11 g/cm$^3$.

The lower layer core 34 containing the fluff pulp at the density in the range as has been specified above ensures that the excretion rapidly spreads in the direction of thickness as well as over the surface of the lower layer core 34 and then is rapidly absorbed by the lower layer core 34. In this way, the amount of excretion having moved through the topsheet 31 and the water-pervious sheets 35 to the lower layer core 34 rapidly spreads entirely over an area 34c of the lower layer core 34 defined between the upper layer cores 33, 33 and almost simultaneously is absorbed by the lower layer core 34 entirely over the area 34c.

In the course of spreading over the area 34c of the lower layer core 34, the amount of excretion having reached the upper layer cores 33, 33 is successively absorbed by these upper layer cores 33, 33 without any possibility of leaking sideways beyond the side edges 30a, 30a of the pad 30. In the upper layer cores 33, 33 containing the fluff pulp at a density lower than that in the lower layer core 34, the amount of excretion having been absorbed by the upper layer cores 33, 33 are then absorbed by the lower layer core 34 and therefore it is not apprehended that the amount of excretion might exude from the upper layer cores 33, 33 even when these upper layer cores 33, 33 are collapsed under a wearer's body weight.

The upper layer cores 33, 33 containing the fluff pulp at the range of density are more soft than the lower layer core 34 and do not give the wearer a feeling of discomfort as these upper layer cores 33, 33 come in contact with the wearer's skin. The reason for which the fluff pulp content density in the upper layer cores 33, 33 and the lower layer core 34 are selected with the respective ranges is the same as in the case of the diaper shown in FIG. 1.

The upper and lower layer cores 33, 33, 34 may contain, in addition to the fluff pulp and the high molecular water-absorbent polymer, staple fibers made of thermoplastic synthetic resin. The upper layer cores 33, 33 contain the fluff pulp and staple fibers at a density lower in the lower layer core 34. Preferably, the upper layer cores 33, 33 contain the fluff pulp and the staple fibers as a whole at a density of 0.02~0.10 g/cm$^3$ and the lower layer core 34 contains them at a density of 0.05~0.20 g/cm$^3$.

The barrier sheets 35 are folded inward laterally of the pad 30 along the respective side edges 30a, 30a of the pad 30 and each of the barrier sheets 35 has a first portion 35a extending from the side edge 30a of the pad 30 over the outer surface of the topsheet 31 and a second portion 35e extending from the side edge 30a of the pad 30 over the outer surface of the backsheet 32.

The first portion 35a of the barrier sheet 35 has a fixed side edge zone 35b fixed to the outer surface of the topsheet 31 along the apex of the upper layer core 33, a free side edge zone 35c extending parallel to the fixed side edge zone 35b between the longitudinally opposite ends 30b of the pad 30, and fixed end zones 35d laterally outward collapsed and fixed to a portion of the barrier sheet 35 extending laterally outward from the fixed side edge zone 35b. A longitudinally extending elastically stretchable member 37 is bonded with tension to the free side edge zone 35c so that the member 37 is wrapped with the outermost portion of the free side edge zone 35c. The second portions 35e are fixed to the outer surface of the backsheet 32 along the side edges 30a and the longitudinally opposite ends 30b of the pad 30.

The fixed side edge zones 35b, 35b of the respective leak-proof sheets 35, 35 lie on the apices of the respective upper layer cores 33, 33. Such a unique arrangement allows the upper layer cores 33, 33 to cooperate with the free side edge zones 35b, 35b of the respective barrier sheets 35, 35 to form sufficiently high barriers to prevent the excretion from leaking sideways.

In the proximity of the longitudinally opposite ends 30b of the pad 30, the backsheet 32 is provided on its outer surface with a pair of male mechanical fasteners 38, 38 adapted to be anchored on the inner surface of the outer member.

FIG. 4 illustrates the pad 30 as being longitudinally curved with its inner surface inside so that the free side edge zones 35b, 35b of the respective barrier sheets 35, 35 may rise on the outer surface of the topsheet 2 under contraction of the elastic members 37 provided on these free side edge zones 35b, 35b. Contraction of the respective elastic members 37 generates gathers along the free side edge zones 35b, 35b.

In the vicinity of the transversely opposite side edges 30a, 30a of the pad 30, the top- and backsheets 31, 32 extend laterally outward beyond transversely opposite side edges 33a, 33a of the lower layer core 34 and, in extensions of these sheets 31, 32 placed one upon another, the inner surface of the topsheet 31 is joined to the inner surface of the backsheet 32.

In the vicinity of the longitudinally opposite ends 30b, 30b of the pad 30, the top- and backsheets 31, 32 extend longitudinally outward beyond longitudinally opposite ends 33b, 33b of the lower layer core 34 and, in their extensions placed upon each other, the inner surface of the topsheet 31 is joined to the inner surface of the backsheet 32. The water-pervious sheet 36 covering each of the upper layer cores 33, 33 is joined to the inner surface of the topsheet 31 and the water-pervious sheet 36 covering the lower layer core 34 is joined to the inner surface of the backsheet 32.

The core 4 of the diaper 1 shown in FIG. 1 may contain different amounts of polymer in the protruding zones 4c, 4c and the zone 4b. Also in the case of the pad 30 shown in FIG. 6, the core assembly 33, 34 may contain different amounts of polymer in the upper layer cores 33, 33 and the lower layer core 34.

Now it is assumed that the polymer particles content depends on the individual zones or the individual cores. The core of FIG. 1 contains the polymer particles at a density lower in its protruding cones 4c, 4c than in the zone 4d wherein the protruding zones 4c, 4c contain the fluff pulp and the polymer particles as a whole preferably at a density of 0.02~0.10 g/cm$^3$ and the zone 4d contains them as a whole preferably at a density of 0.05~0.20 g/cm$^3$. In the case of the core 4 containing the staple fibers also, the protruding zones 4c, 4c contain the fluff pulp, the polymer particles and the staple fibers as a whole preferably at a density of 0.02~0.10 g/cm$^3$ and the zone 4d contains them as a whole preferably at a density of 0.05~0.20 g/cm$^3$.

Similarly, the core assembly 33, 34 of FIG. 6 contains the polymer particles at a density lower in the upper layer cores 33, 33 than in the lower layer core 34 wherein the upper layer cores 33 contain the fluff pulp and the polymer particles as a whole preferably at a density of 0.021~0.10 g/cm$^3$ and the lower layer core 34 contains them as a whole preferably at a density of 0.05~0.20 g/cm$^3$. For the case in which both the upper layer cores 33, 33 and the lower layer core 34 contain the staple fibers also, the upper layer cores 33, 33 contain the fluff pulp, the polymer particles and the staple fibers as a whole preferably at a density of 0.02~0.10 g/cm$^3$ and the lower layer core 34 contains them as a whole preferably at a density of 0.05~0.20 g/cm$^3$.

For the case in which the core 4 of FIG. 1 and the core assembly 33, 33, 34 of FIG. 6 contain the polymer particles of which the respective amounts depend on the individual zones or the individual cores, the polymer particles density in each of the zones or cores may have a predetermined gradient. In the core 4 of FIG. 1, a gradient is preferably provided so that the polymer particles density may progressively increase from the upper part toward the lower part of the protruding zone 4c. In the core assembly 33, 33, 34 of FIG. 6 also, a gradient is preferably provided so that the polymer particles density may progressively increase from the upper parts of the upper layer cores 33, 33 toward the lower part of the lower layer core 34. It should be understood here that the zone 4d of the core 4 as well as the lower layer core 34 may be realized also in the form of laminates consisting of the polymer particles layer sandwiched between the fluff pulp layers rather than in the form of the mixture of the fluff pulp and the polymer particles.

Since the core 4 of FIG. 1 comprises the protruding zones 4c, 4c integrally formed with the zone 4d, a process for making the core 4 must include a step of generating a differential density between the protruding zones 4c, 4c and the zone 4d. In the contrast with this, the core assembly 33, 33, 34 of FIG. 6 is more advantageous than the core 4 of FIG. 1 from the viewpoint of the manufacturing cost. This is for the reason that the core assembly 33, 33, 34 is formed merely by assembling the upper layer cores 33, 33 and the lower layer core 34 prepared separately without needs for the step as required by the core 4 of FIG. 1.

In the core 4 of FIG. 1 as well as in the core assembly 33, 33, 34 of FIG. 6, the protruding zones 4c, 4c and the upper layer cores 33, 33 preferably have a vertical dimension of 3~15 mm, more preferably, of 7~8 mm. The zone 4d and the lower layer core 34 preferably have a vertical dimension of 1~10 mm, more preferably, of 3~4 mm.

The high molecular water-absorbent polymer particles are preferably of a granular gelling type capable of absorbing and holding liquid 20-times or more of its own weight and may be selected from a group consisting of starch-acrylate graft polymer, saponificated starch-acrylonitrile copolymer, crosslinked sodium carboxymethyl cellulose and acrylate polymer.

The topsheet 2, 31 may be formed by a liquid-pervious sheet such as a nonwoven fabric or porous plastic film, preferably by a liquid-pervious hydrophilic sheet. The backsheet 5, 35 may be formed by a hydrophobic nonwoven fabric, liquid-impervious plastic film or a laminated sheet of hydrophobic nonwoven fabric and plastic film, preferably by a breathable liquid-impervious sheet. The water-pervious sheet 6, 36 covering the core 4, 33, 34 may be a tissue paper or liquid-pervious nonwoven fabric having a basis weight of 5~10 g/m$^2$.

The nonwoven fabric may be selected from a group including a spun lace nonwoven fabric, needle punch nonwoven fabric, melt blown nonwoven fabric, thermal bond nonwoven fabric, spun bond nonwoven fabric and chemical bond nonwoven fabric. Component fiber of the nonwoven fabric and staple fiber contained in the core may be selected from a group including polyolefine, polyester and polyamide fibers, and polyethylene/polypropyrene or polyester conjugated fiber.

Joining and/or attaching of the sheets 2, 3, 5, 6, 31, 32, 35, 36, the component members of the diaper 1 and the pad 30 and the elastic members 7, 8, 11, 37 may be carried out using suitable adhesive such as hot melt adhesive or pressure-sensitive adhesive or a heat-sealing technique.

This invention is applicable, not only to the disposable diaper or the urine-absorbent pad for incontinent but also the diaper liner, panty liner or sanitary napkin.

What is claimed is:

1. A body fluid absorbent garment contoured by transversely opposite and longitudinally extending side edges and longitudinally opposite and transversely extending ends, said garment comprising a basic structure having a liquid-pervious topsheet; a liquid-impervious backsheet and a liquid-absorbent core disposed therebetween;

wherein
   said core comprises a lower core member and two upper core members separate from and placed upon the lower core member, the upper core members being spaced from each other and extending along the respective transversely opposite side edges of said garment;
   each of the upper core members has a density lower than that of the lower core member; and
   said core is thicker in regions where both the lower core member and one of the upper core member are present than in a region where only the lower core member is present.

2. The garment according to claim 1, wherein each of said lower and upper core members contains a mixture of fluff pulp and high molecular water absorbent polymer particles, and said fluff pulp has a density lower in the upper core members than in the lower core member.

3. The garment according to claim 2, wherein each of said lower and upper core members further contains staple fibers made of a thermoplastic synthetic resin, and said fluff pulp and said staple fibers together have a density lower in the upper core members than in the lower core member.

4. The garment according to claim 2, wherein said fluff pulp has the density of from about 0.02 to about 0.10 g/cm$^3$ in the upper core members and of from about 0.05 to about 0.20 g/cm$^3$ in the lower core member.

5. The garment according to claim 2, wherein said polymer particles have a density progressively increasing from an upper part of each of the upper core members towards a lower part of the lower core member.

6. The garment according to claim 2, wherein the lower core member is a laminate of a layer of said polymer particles being sandwiched between layers of said fluff pulp.

7. The garment according to claim 1, wherein an outermost longitudinal edge of each of the upper core member is inwardly spaced from a respective outermost longitudinal edge of the lower core member.

8. The garment according to claim 1, wherein said garment has along a longitudinal direction thereof a front waist section, a rear waist section and a crotch section therebetween, said lower core member has substantially equal areas in the front waist section and the crotch section, and said lower core member has an area in the rear waist section which is larger than the total of the areas thereof in the front waist section and the crotch section.

9. The garment according to claim 1, further comprising a pair of liquid-barrier sheets extending longitudinally of said garment, each of said liquid-barrier sheets having a middle portion being fixed to the topsheet along an upper longitudinal edge portion of one of said upper core members, said liquid-barrier sheet further having on opposite sides of said middle portion a free end portion being elastically stretchable longitudinally of said garment and risable on the topsheet and a fixed end portion being fixed to said basic structure along the respective transversely opposite side edge of said garment.

10. The garment according to claim 9, wherein said fixed end portion extends around the respective transversely opposite side edge of said garment and is fixed to an outer surface of the backsheet.

11. The garment according to claim 1, wherein the lower core member has a substantially uniform thickness through an entire area thereof.

12. A body fluid absorbent garment contoured by transversely opposite and longitudinally extending side edges and longitudinally opposite and transversely extending ends, said garment comprising:

a basic structure having a liquid-pervious topsheet; a liquid-impervious backsheet and a liquid-absorbent core disposed therebetween; and a pair of liquid-barrier sheets extending longitudinally of said garment;

wherein said core includes a central zone and two side barrier zones on opposite sides of the central zone, the side barrier zones spaced from each other and extending along the respective transversely opposite side edges of said garment;

said core has a density which in the side barrier zones is lower than in the central zone;

said core in the side barrier zones is thicker than in the central zone;

each of said liquid-barrier sheets having a middle portion being fixed to the topsheet along an upper longitudinal edge portion of said core in the side barrier zones, said liquid-barrier sheet further having on opposite sides of said middle portion a free end portion being elastically stretchable longitudinally of said garment and risable on the topsheet and a fixed end portion being fixed to said basic structure along the respective transversely opposite side edge of said garment.

13. The garment according to claim 12, wherein said core contains a mixture of fluff pulp and high molecular water absorbent polymer particles, and said fluff pulp has a density in the side barrier zones lower than in the central zone.

14. The garment according to claim 13, wherein said core further contains staple fibers made of a thermoplastic synthetic resin, and said fluff pulp and said staple fibers together have a density in the side barrier zones lower than in the central zone.

15. The garment according to claim 13, wherein said fluff pulp has the density of from about 0.02 to about 0.10 g/cm$^3$ in the side barrier zones and of from about 0.05 to about 0.20 g/cm$^3$ in the central zone.

16. The garment according to claim 13, wherein said polymer particles, in the side barrier zones, have a density progressively increasing from an upper part of said core towards a lower part thereof.

17. The garment according to claim 13, wherein said polymer particles are distributed substantially uniformly throughout said core.

18. The garment according to claim 13, wherein the central zone of said core is a laminate of a layer of said polymer particles being sandwiched between layers of said fluff pulp.

19. The garment according to claim 12, wherein said fixed end portion extends around the respective transversely opposite side edge of said garment and is fixed to an outer surface of the backsheet.

20. The garment according to claim 12, wherein each of the side barrier zones is defined by a raised portion of said core, said raised portion is curved laterally inwardly of said garment as said raised portion extends along the respective transversely opposite side edge of said garment.

21. The garment according to claim 12, wherein each of the side barrier zones is defined by a raised portion of said core, said raised portion is curved laterally outwardly of said garment as said raised portion extends along the respective transversely opposite side edge of said garment.

22. The garment according to claim 12, wherein said core further includes end barrier zones extending along longitudinally opposite ends of said garment and connecting the side barrier zones, said end and side barrier zones together describe a loop-shaped barrier zone.

* * * * *